United States Patent
Sharrock

(10) Patent No.: US 8,606,528 B2
(45) Date of Patent: Dec. 10, 2013

(54) ASSAY DEVICE

(75) Inventor: Stephen Paul Sharrock, Bedford (GB)

(73) Assignee: SPD Swiss Precision Diagnostics GmbH (CH)

( * ) Notice: Subject to any disclaimer, the term of this patent is extended or adjusted under 35 U.S.C. 154(b) by 321 days.

(21) Appl. No.: 12/995,346

(22) PCT Filed: May 29, 2009

(86) PCT No.: PCT/GB2009/050590
§ 371 (c)(1),
(2), (4) Date: Feb. 22, 2011

(87) PCT Pub. No.: WO2009/144507
PCT Pub. Date: Dec. 3, 2009

(65) Prior Publication Data
US 2012/0072125 A1   Mar. 22, 2012

(30) Foreign Application Priority Data

May 31, 2008   (GB) .................................. 0809995.4

(51) Int. Cl.
*G01N 33/50* (2006.01)
*G01N 33/48* (2006.01)

(52) U.S. Cl.
USPC .......................................................... 702/19

(58) Field of Classification Search
None
See application file for complete search history.

(56) References Cited

U.S. PATENT DOCUMENTS

| | | | |
|---|---|---|---|
| 2005/0037510 A1 * | 2/2005 | Sharrock et al. | 436/164 |
| 2005/0112779 A1 | 5/2005 | Wei et al. | |
| 2007/0185679 A1 | 8/2007 | Petruno et al. | |

FOREIGN PATENT DOCUMENTS

| | | |
|---|---|---|
| EP | 291194 A1 | 11/1988 |
| EP | 1484613 A2 | 12/2004 |
| EP | 2031376 A2 | 3/2009 |
| WO | WO-0005571 A1 | 2/2000 |
| WO | WO-2005051170 A2 | 6/2005 |
| WO | WO-2005052716 A1 | 6/2005 |
| WO | WO-2008122796 A1 | 10/2008 |

OTHER PUBLICATIONS

International Search Report and Written Opinion for PCT/GB2009/050590 dated Apr. 8, 2009.
International Search Report for PCT/GB2009/050590 mailed Aug. 4, 2009.

* cited by examiner

*Primary Examiner* — Jason Sims
(74) *Attorney, Agent, or Firm* — Foley Hoag LLP

(57) ABSTRACT

Disclosed is an assay result reading apparatus, for reading the result of an assay, comprising: a) first and second control thresholds; b) a data processing means for processing an analyte measurement signal indicative of the presence and/or amount of an analyte; and for processing a control signal indicative of whether the assay has been carried out satisfactorily; to: up until a time $t_1$ after commencement of the assay measurement, to compare the control signal with the first control threshold and determine that the assay has been carried out satisfactorily if the control signal exceeds or is equal to the first control threshold, and if the control signal is less than the first control threshold to continue the assay measurement; and at a time $t > t_1$ to compare the control signal with a second control threshold and provide an assay result if the control signal exceeds or is equal to the second control threshold.

26 Claims, 5 Drawing Sheets

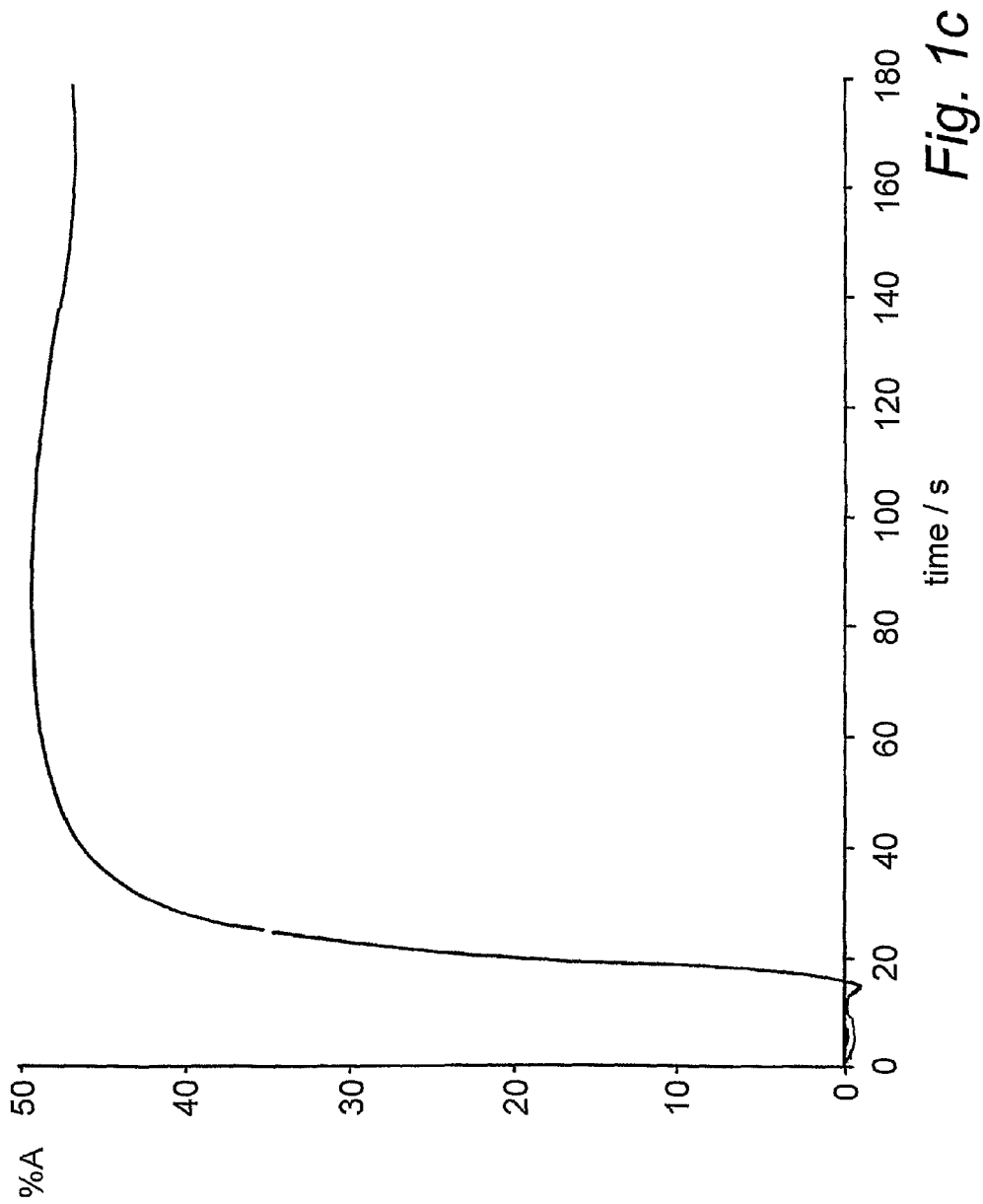

ASSAY DEVICE

This application is a 371 national stage application of PCT/GB2009/050590, filed May 29, 2009, which claims priority to GB 0809995.4, filed May 31, 2008. The entire contents of each of these applications are hereby incorporated by reference.

FIELD OF THE INVENTION

The present invention relates to an assay device, kit and method for determining the presence or extent of an analyte.

BACKGROUND OF THE INVENTION

Simple lateral flow immunoassay devices have been developed and commercialised for detection of analytes in fluid samples, see for example EP291194. Such devices typically comprise a porous carrier comprising a dried mobilisable labelled binding reagent capable of binding to the analyte in question, and an immobilised binding reagent also capable of binding to the analyte provided at a detection zone downstream from the labelled binding reagent. Detection of the immobilised labelled binding at the detection zone provides an indication of the presence of analyte in the sample. The assay device may additionally incorporate a control zone to indicate that the test has been carried out satisfactorily. The control zone is typically positioned downstream from the detection zone and may comprise an immobilised binding reagent for a labelled binding reagent.

EP1484613 discloses an electronic assay device for the determination of an analyte comprising an optical detection means wherein said assay measures signals from an analyte measurement zone over time with respect to one or more thresholds and provides a result to the user.

A sandwich immunoassay is often the immunoassay assay of choice when detecting analytes. However, a sandwich assay is not always possible, for example in the case of small molecules such as haptens which may not be large enough to allow the simultaneous binding thereto of two different binding partners. A dose-response curve prepared using a typical lateral flow device employing a sandwich immunoassay shows increasing levels of signal with increasing analyte up to the point where at higher analyte levels the curve tends to plateau. At yet higher analyte levels, the signal begins to decrease due to preferential capture at the detection zone of analyte which has not yet bound to labelled reagent. This phenomenon is known as the hook effect. Thus sandwich immunoassays exhibit a limited assay range due to the fact that the signal amount or intensity observed at higher analyte levels may be the same, or even less, than that observed at lower analyte levels.

Thus in order to detect analytes at higher concentrations, especially in other than a qualitative manner, it is necessary to employ alternative methods or assay devices.

WO2005052716 discloses an assay device for the detection of an analyte at high concentration levels wherein the assay device comprises a scavenging zone comprising capture reagent capable of binding to the analyte. This has the effect of preventing some of the analyte from being detected at a detection zone and lowers the sensitivity of the assay.

SUMMARY OF THE INVENTION

It is an object of the invention to provide an assay device for the detection of an analyte having an improved control. In particular it is an object to provide an assay device having an improved control for the detection of an analyte over an extended concentration range.

According to a first aspect, the invention provides an assay reading apparatus for determining the result of an assay, the apparatus comprising:
a) first and second control thresholds;
b) a data processing means for processing an analyte measurement signal indicative of the presence and/or amount of an analyte; and for processing a control signal indicative of whether the assay has been carried out satisfactorily; to:
   up until a time $t_1$ after commencement of the assay measurement, compare the control signal with the first control threshold and determine that the assay has been carried out satisfactorily if the control signal exceeds or is equal to the first control threshold, and if the control signal is less than the first control threshold to continue the assay measurement; and at a time $t>t_1$ to compare the control signal with a second control threshold and provide an assay result if the control signal exceeds or is equal to the second control threshold.

According to a second aspect, the invention provides an assay device for providing the presence and/or amount of an analyte in a liquid sample comprising:
a) an assay result reading apparatus according to the first aspect of the invention; and,
b) one or more assay flow-paths along which a liquid sample may flow, said one or more flow paths comprising:
   a detection zone for immobilising a labelled binding reagent indicative of the presence and/or amount of the analyte; and
   a control zone for indicating that assay has been carried out satisfactorily.

According to a third aspect, the invention provides a method of determining the result of an assay comprising:
a) measuring an analyte measurement signal indicative of the presence and/or amount of an analyte and a control signal indicative of whether the assay has been carried out satisfactorily;
b) up until a time $t_1$ after commencement of the assay measurement, determining that the assay has been carried out correctly if the control signal exceeds or is equal to a first control threshold and if the control signal is less than the first control threshold to continue the assay signal measurement; and at a time $t>t_1$ to compare the control signal with a second control threshold and provide an assay result if the control signal exceeds or is equal to the second control threshold.

The assay reader, device and method according to the first, second and third aspects of the invention may comprise a first measurement threshold wherein the analyte measurement signal is compared to the measurement threshold and an assay result is provided if the analyte measurement signal is equal to or greater than the measurement threshold. The assay result may be provided at a time $t<t_{fd}$, wherein $t_{fd}$ is the full development time of the assay, namely the maximum time over which the assay is measured.

The assay result may be provided only after a minimum assay development time, $t_{md}$ has elapsed. $T_{md}$ may be zero.

Thus, if the analyte measurement signal exceeds or is equal to the measurement threshold and if the control signal exceeds or is equal to the first control threshold, an assay result may be provided early, namely at a time less than the full development time of the assay.

The measurement threshold is indicative of a certain concentration or level of analyte. The measurement threshold may be indicative of a zero level of analyte.

According to an embodiment, the control signal is compared to the second control threshold at $t_{fd}$, and at any time $t<t_{fd}$, the control signal is compared to the first control threshold.

During the course of the assay, the control and analyte measurement signals may be measured continuously. Up until a time $t_1$ after commencement of the assay measurement, if the control signal exceeds or is equal to the first control threshold, the assay result reader or device checks to see whether the measurement signal has exceeded or is equal to the measurement threshold, in which case an early assay result, is provided. If the control signal does not exceed the first control threshold, the assay device continues to monitor the control signal and an early result is not provided until the control signal exceeds or is equal to the first control threshold, even if the measurement signal is greater than the measurement threshold. At assay times $t>t_1$, the control signal is compared to the second control threshold and an assay result is provided if the control signal is greater than or equal to the second control threshold. If the control signal is less than the second control threshold, the assay device provides an indication that the assay has not been carried out correctly.

The first and second control thresholds differ from one another. The first control threshold may be greater than the second control threshold. The value chosen for the control thresholds may vary and will depend upon the particular assay and the analyte to be determined.

The assay result reading apparatus, device and method according to the first, second and third aspects of the invention may further comprise a minimum analyte threshold wherein if the measurement signal is less than the minimum threshold by a minimum analyte threshold time, $t_{ma}$, it is determined that the measurement signal will never reach the measurement threshold by the full assay development time. This would represent the case of a liquid sample having a very low or non-existent analyte concentration. In this case an early negative indication, namely an indication of the absence of analyte or the absence of analyte above a certain minimum level, may be provided at a time $t<t_{fd}$.

The assay result reading apparatus, device and method according to the first, second and third aspects of the invention may comprise more than two control thresholds. As an alternative to providing first and second thresholds, the assay result reading apparatus, device and method according to the first, second and third aspects of the invention may comprise a variable control threshold whose value changes during the course of the assay measurement.

Thus according to fourth aspect of the invention, there is provided an assay result reading apparatus, for reading the result of an assay, the apparatus comprising:
a) a variable control threshold whose value varies over the time of the assay measurement;
b) a data processing means for processing an analyte measurement signal over time indicative of the presence and/or amount of an analyte; and for processing a control signal over time indicative of whether the assay has been carried out satisfactorily; to, at any particular time during measurement of the assay, compare the control signal with the variable control threshold and determine that the assay has been carried out satisfactorily if the control signal exceeds or is equal to the variable control threshold.

According to a fifth aspect there is provided an assay device for providing the presence and/or amount of an analyte in a liquid sample, the apparatus comprising:
a) an assay result reading apparatus according to the fourth aspect; and
b) one or more flow-paths along which a liquid sample may flow, said one or more flow paths comprising:
a detection zone for immobilising a labelled binding reagent indicative of the presence and/or amount of the analyte; and
a control zone for indicating that assay has been carried out satisfactorily.

The assay device may comprise a mobilisable labelled binding reagent which is capable of being immobilised at the detection zone. The reagent may be provided upstream from the detection zone. The labelled binding reagent may be provided in the dry state.

The detection zone may comprise an immobilised binding reagent which is capable of immobilising a labelled binding reagent.

Alternatively, the assay device may comprise mobilisable labelled binding and second binding reagents, wherein a reagent may be provided in an immobilised form at a detection zone that is capable of binding a mobilisable labelled binding reagent-analyte-second binding reagent complex, wherein the second binding reagent is capable of binding to both analyte and to the immobilised reagent. For example the reagent immobilised at the detection zone may be a binding partner such as streptavidin or anti-biotin, such that an immobilised labelled binding reagent-analyte-second binding reagent complex (e.g. biotin—streptavidin complex) is formed at the detection zone.

Alternatively the detection zone may comprise a filter which is capable of immobilising a mobilisable labelled binding reagent—analyte—second binding reagent complex. The filter is of dimensions such that labelled binding reagent is able to pass through the filter and the second binding reagent may be labelled with a particle which is unable to pass the filter such that the filter is able to trap the any labelled binding reagent-analyte-second binding reagent complex present, any labelled binding reagent that is not complexed to the capture reagent being able to pass through the filter.

Measurement of the signal at the control zone indicates whether the assay test has been carried out satisfactorily, namely the reagents were present in the test device and that they become mobilised during the running of the test and have been transported along the flow path. The control zone can also indicate that the reagents within the device are capable of immunochemical interactions, confirming the chemical integrity of the device. This is important when considering the storage and shipment of the device under desiccated conditions within a certain temperature range. The control zone is typically positioned downstream from the detection zone. The control zone may comprise immobilised binding reagent for a labelled binding reagent. The labelled binding reagent may be the same binding reagent that binds to the detection zone or it may be a different binding reagent. The immobilised binding reagent at the control zone may for example be an anti-species antibody to a labelled binding reagent raised in a species, e.g. an "anti-mouse" antibody if the labelled antibody is one that has been derived using a murine hybridoma.

The term "binding reagent" refers to a member of a binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the specific binding pair are referred to as ligand and receptor (antiligand), a binding pair member and binding pair partner, and the like. A molecule may also be a binding pair member for an aggregation of molecules; for example an antibody raised against an immune complex of a second antibody and its corresponding antigen may be considered to be a binding pair member for the immune complex. The binding reagent may comprise an antibody or an antibody fragment, capable of binding to an antigen.

In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogues of the original specific binding member.

"Label" when used in the context of a labelled binding reagent, refers to any substance which is capable of producing a signal that is detectable by visual or instrumental means. Various labels suitable for use in the present invention include labels which produce signals through either chemical or physical means, such as being optically detectable. Such labels include enzymes and substrates, chromogens, catalysts, fluorescent compounds, chemiluminescent compounds, electroactive species, dye molecules, radioactive labels and particle labels. The analyte itself may be inherently capable of producing a detectable signal. The label may be covalently attached to the binding reagent.

The label may comprise a particle such as gold, silver, colloidal non-metallic particles such as selenium or tellurium, dyed or coloured particles such as a polymer particle incorporating a dye, or a dye sol. The dye may be of any suitable colour, for example blue. The dye may be fluorescent. Dye sols may be prepared from commercially-available hydrophobic dyestuffs such as Foron Blue SRP (Sandoz) and Resolin Blue BBLS (Bayer). Suitable polymer labels may be chosen from a range of synthetic polymers, such as polystyrene, polyvinyltoluene, polystyrene-acrylic acid and polyacrolein. The monomers used are normally water-insoluble, and are emulsified in aqueous surfactant so that monomer micelles are formed, which are then induced to polymerise by the addition of initiator to the emulsion. Substantially spherical polymer particles are produced. According to an exemplary embodiment the label is a blue polymeric particle.

The term "assay flow-path" refers to a substrate that is able to convey a liquid from a first position to a second position and may be for example a capillary channel, a microfluidic pathway, or a porous carrier such as a lateral flow porous carrier. The porous carrier may comprise one or a plurality of porous carrier materials which may overlap in a linear or stacked arrangement or which are fluidically connected. The porous carrier materials may be the same or different. The first and second flow paths may be provided on separate substrates or they may be provided on a common substrate such that liquid being conveyed along a flow-path of the first assay is not able to cross over to the flow-path of the second assay. For example, the first and second assays may be provided on the same porous carrier such that the first and second flow-paths are isolated from each other. This may be achieved for example by laser cutting parts of the porous carrier to make it non-porous, thus separating the first and second flow-paths. As yet a further alternative, the first and second detection zones may be provided on the same flow-path in substantially a side by side arrangement, such that neither is provided downstream from the other.

In particular the flow-path may comprise a lateral flow porous carrier. The labelled binding reagent and detection zone of the assay may be provided respectively on different carrier materials. Suitable materials that may be employed as a porous carrier for providing the detection zone include nitrocellulose, acetate fibre, cellulose or cellulose derivatives, polyester, polyolefin or glass fibre. The porous carrier may comprise nitrocellulose. This has the advantage that a binding reagent can be immobilised firmly without prior chemical treatment. If the porous solid phase material comprises paper, for example, the immobilisation of the antibody in the second zone needs to be performed by chemical coupling using, for example, CNBr, carbonyldiimidazole, or tresyl chloride.

The assay flow-path may be provided in the form of a test-strip.

The liquid sample can be derived from any source, such as an industrial, environmental, agricultural, or biological source. The sample may be derived from or consist of a physiological source including blood, serum, plasma, interstitial fluid, saliva, sputum, ocular lens liquid, sweat, urine, milk, mucous, synovial liquid, peritoneal liquid, transdermal exudates, pharyngeal exudates, bronchoalveolar lavage, tracheal aspirations, cerebrospinal liquid, semen, cervical mucus, vaginal or urethral secretions and amniotic liquid. In particular the source is human and in particular the sample is urine.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof.

The assay device and reader may comprise one or more of the following: a central processing unit (CPU) or microcontroller; one or more LED's; one or more photodetectors; a power source; and associated electrical circuitry. The power source may be a battery or any other suitable power source (e.g. a photovoltaic cell). Conveniently the CPU or microcontroller will be programmed so as determine, from the output of the photodetectors, the rate or amount of signal accumulation and to compare this to the control and measurement thresholds.

The assay device and reader comprises a timing means by which to measure the time of the assay and by which to determine the time of commencement of measurement of the assay. The timing means may for example comprise a sample presence indication means to detect the time at which liquid sample is added to the device such as a pair of electrodes which are able to detect the presence of liquid sample. Alternatively the timing means may be comprised as part of the optical detection means, wherein timing of the assay measurement is commenced at the time liquid sample is determined by the photodetector as having reached a particular detection or reference zone.

The assay device and display may further comprise a display means to display the result of the assay. The display means may further display further information such as an error massage, personal details, time, date, and a timer to inform the user how long the assay has been measured for. The information displayed by the assay may be indicated in words, numbers or symbols, in any font, alphabet or language, for example, "positive", "negative", "+", "−", "pregnant", "not pregnant", "see your doctor", "repeat the test".

The assay device comprises a signal detection means to determine the extent and/or amount of labelled species present at the detection and control zones. The signal detection means may comprise an optical detection means such as a photodetector to determine the extent and/or amount of labelled species present. The assay device may comprise one or more light sources such as an LED positioned so as to optically illuminate the zones. Light from the light source illuminates the respective zones and is either transmitted or reflected onto a photodetector which records the amount or intensity of the transmitted or reflected light. The presence of labelled binding reagent at the zones will influence the amount of light that is either transmitted or reflected, thus measurement of light at the photodetector is indicative of the presence or amount of the labelled binding reagent.

The assay device may further comprise a reference zone. The purpose of the reference zone is to provide a signal value against which the signal values obtained at the detection and control zones may be compared. Measurement of the reference zone enables measurement of the background levels of reflected or transmitted light from the flow-path. The background level may be due for example to the optical reflectance of the porous carrier, the presence of liquid sample, or of components of the assay such as a labelled binding reagent. The levels of light measured at the detection zone may therefore be corrected with respect to the levels of background light to provide a compensated signal indicative of the amount of labelled binding reagent present at the detection zone. Measurement at the reference zone may also compensate for any variation between fluid samples applied to assay devices, for example urine samples may vary widely in colour.

A suitable light source is an LED. The colour of the LED will be determined by the colour of the labelled binding reagent. For a blue label, a suitable colour for the LED is red. The LED may be illuminated at a particular frequency or frequencies in order to illuminate a particular zone of the assay device. Light is reflected or transmitted from the zone onto a photodetector which records an electrical signal. The number of electrical signals recorded will depend upon the operating frequency of the LED and thus one or more signals may be recorded over time. The signals will typically be expressed as a % absorbance (% A).

Each measurement zone is typically illuminated by a single LED. A photodetector may detected light from one than one measurement zone and therefore reflected light from one than one LED. This may be achieved by carrying out the illumination process sequentially such that device is able to know which from which zone light is being reflected from onto the photodetector. The sequential illumination process may be repeated with a fixed or varied frequency during the duration of the assay such that the levels of signal over time at each zone may be monitored.

The device may comprise a means to detect the time addition of flow to the assay device. For example, the change in levels of light detected from one or more zones may be monitored to determine whether and when a fluid sample has been applied to the device. The timing of the assay test may be started automatically for example when liquid sample has reached a particular zone.

The device may comprise a flow control means wherein the change in levels of light detected from one or more zones may be used to determine whether and when a fluid sample has been applied to the device and to determine the flow-rate of liquid sample along the device by measurement of flow between one or more measured zones. Determination of the flow-rate may be used as a further quality control check, for example the assay may be rejected if the flow-rate is either greater than or less than set levels. The computation circuit may be responsive to the signals to calculate a flow rate for a fluid flowing along the carrier, compare the calculated flow rate to upper and lower limits, and reject the assay result if the calculated flow rate is outside the upper and lower limits.

The typical optical detection system will comprise at least one light source and at least one photodetector (such as a photodiode). Preferred light sources are light emitting diodes or LEDs. Reflected light and/or transmitted light may be measured by the photodetector. For the purposes of this disclosure, reflected light is taken to mean that light from the light source is reflected from the porous carrier or other liquid transport carrier onto the photodetector. In this situation, the detector is typically provided on the same side of the carrier as the light source. Transmitted light refers to light that passes through the carrier and typically the detector is provided on the opposite side of the carrier to the light source. For the purposes of a reflectance measurement, the carrier may be provided with a backing such as a white reflective MYLAR® plastic layer. Thus light from the light source will fall upon the carrier, some will be reflected from its surface and some will penetrate into the carrier and be reflected at any depth up to and including the depth at which the reflective layer is provided. Thus, a reflectance type of measurement may actually involve transmission of light through at least some of the thickness of the porous carrier.

The assay device will typically comprise one or more apertures or windows through which light may shine from the one of more sources of illumination onto a particular zone of the assay or assay strip. The windows serve to define the area of light falling onto a particular zone and to define which part of the assay or assay strip is illuminated. Each zone to be illuminated may have a corresponding window. Thus a device having four measurement zones will have four windows. Light reflected from the windows is collected by the one or more photodetectors. For an assay device comprising a flow path having a plurality of zones the time taken for the liquid sample to travel between the zones may be measured.

Measurements of the light reflected from each window may be taken periodically (for example approximately twice a second) and a low pass digital filter may be used to reject noise and smooth the data. Filtered values may be used for detecting flow and determining the assay result.

For each window, a ratio may be calculated of the measured value when the particular measurement zone in the flow-path is dry ("calibration value"), namely before any liquid sample has reached said zone, divided by the measured value when the measurement zone is wet and a line may have developed. This ratio equals the proportion of light reflected after the change in the reflective properties of the flow-path as a consequence of the liquid sample passing along the flow-path. For example when the flow-path comprises a porous carrier such as nitrocellulose the change in reflective properties can be quite marked.

For each window, the window ratio at the reference, control, and test windows is equal to the measured value when the porous carrier is dry, t=0 (prior to addition of sample), divided by the measured value at time t after addition of sample:

For each time point t the window ratios for each window may be evaluated as follows:

$$Ref\ ratio_t = \frac{\text{filtered reference window } value_{time=0}}{\text{filtered reference window } value_{time=t}}$$

$$\text{Test ratio}_t = \frac{\text{filtered test window } value_{time=0}}{\text{filtered test window } value_{time=t}}$$

$$\text{Ctrl ratio}_t = \frac{\text{filtered Ctrl window } value_{time=0}}{\text{filtered Ctrl window } value_{time=t}}$$

Calculation of Filtered % A Values

For each time point t. % A values may calculated using these ratios for a test line and a control line using the reference ratio as a baseline for the background that would have occurred in all windows had a line not developed.

$$\text{Test}_t(\% \ A) = \frac{\text{Ref ratio}_t - \text{test ratio}_t}{\text{Ref ratio}_t} \times 100\%$$

$$\text{Ctrl}_t(\% \ A) = \frac{\text{Ref ratio}_t - \text{Ctrl ratio}_t}{\text{Ref ratio}_t} \times 100\%$$

The filtered % A value may be defined as follows:

$$(\% \ A) = \frac{\text{Ref ratio}_t - \text{test ratio}_t}{\text{Ref ratio}_t} \times 100\%$$

The normalised percentage relative attenuation (% A) is given by the difference of the reference window ratio and the window ratio being considered (control or test windows) divided by the reference window ratio and multiplied by 100%.

Typically the % A values will be those obtained at the full assay development time.

Control and measurement signal values may be presented as % A, namely the signal value with respect to the signal measured at a reference zone.

Alternatively, signal values may be presented as % R, namely an absolute value.

Flow Detection and Validation

Flow Detection

The window ratio for each window may be used to detect the flow of fluid past the window. Flow is classed as having reached a window when the ratio has dropped by the Flow Detection Threshold Percentage (FDT %). This corresponds to an increase in the filtered value over its calibration value by the same proportion.

For time t, $$\text{Window ratio} \geq \frac{1}{1 + FDT \ \%} \text{ or}$$

$$\frac{\text{filtered value}_{time=t}}{\text{filtered value}_{time=0}} \geq 1 + FDT \ \%$$

The time for each window when the criterion is first satisfied is recorded for flow validation.

Flow Validation

Various parameters corresponding to flow may be stored within the device and used to classify flow of liquid sample along porous carrier of an assay device. The device may display any errors in flow as a consequence of using the device.

The device may comprise one or more of a stored minimum flow detection time, $FDT_{min}$, a maximum flow detection time, $FDT_{max}$, a minimum window transit time $MTT_{min}$ and a flow detection threshold, FDT.

The assay device may comprise a porous sample receiver in fluid connection with and upstream from the flow-path. The assay device may comprise more than one assay flow-path each comprising a detection zone, in which case a single porous sample receiver may be provided which is common to the multiple assay flow paths. Thus a fluid sample applied to the porous sample receiver of the device is able to travel along the flow-paths of the respective assays to the respective detection zones. The porous sample receiver may be provided within a housing or may at least partially extend out of said housing and may serve for example to collect a urine stream. The porous sample receiver may act as a fluid reservoir. The porous sample receiving member can be made from any bibulous, porous or fibrous material capable of absorbing liquid rapidly. The porosity of the material can be unidirectional (i.e. with pores or fibres running wholly or predominantly parallel to an axis of the member) or multidirectional (omnidirectional, so that the member has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. Other suitable materials include glass-fibre.

If desired, an absorbent "sink" can be provided at the distal end of the carrier material. The absorbent sink may comprise of, for example, Whatman 3MM chromatography paper, and should provide sufficient absorptive capacity to allow any unbound labelled binding reagent to wash out of the detection zone. As an alternative to such a sink it can be sufficient to have a length of porous solid phase material which extends beyond the detection zone.

Following the application of a binding reagent to a detection zone, the remainder of the porous solid phase material may be treated to block any remaining binding sites. Blocking can be achieved by treatment for example with protein (e.g. bovine serum albumin or milk protein), or with polyvinylalcohol or ethanolamine, or combinations thereof. To assist the free mobility of the labelled binding reagent when the porous carrier is moistened with the sample, the porous carrier may further comprise a sugar such as sucrose or lactose and/or other substances, such as polyvinyl alcohol (PVA) or polyvinyl pyrrolidone (PVP). Such material may be deposited for example as an aqueous solution in the region to which the labelled binding reagent is to be applied. Such materials could be applied to the porous carrier as a first application followed by the application of the label, alternatively such materials could be mixed with the label and applied to the porous carrier or combinations of both. Such material may be deposited upstream from or at the labelled binding reagent.

Alternatively, the porous carrier may not be blocked at the point of manufacture; instead the means for blocking the porous carrier are included in a material upstream from the porous carrier. On wetting the test strip, the means for blocking the porous carrier are mobilised and the blocking means flow into and through the porous carrier, blocking as the flow progresses. The blocking means include proteins such as BSA and casein as well as polymers such as PVP, PVA as well as sugars and detergents such as Triton—X100. The blocking means could be present in the macroporous carrier material.

The nitrocellulose porous carrier may have a pore size of at least about 1 micron, for example greater than about 5 microns, and for example about 8-12 microns.

The nitrocellulose porous carrier may be backed e.g. with a plastics sheet, to increase its handling strength. This can be manufactured easily by forming a thin layer of nitrocellulose on a sheet of backing material such as Mylar™.

The dried binding reagents may be provided on a porous carrier material provided upstream from a porous carrier material comprising the detection zone. The upstream porous carrier material may be macroporous. The macroporous carrier material should be low or non-protein-binding, or should be easily blockable by means of reagents such as BSA or PVA, to minimise non-specific binding and to facilitate free movement of the labelled reagent after the macroporous body has become moistened with the liquid sample. The macroporous carrier material can be pre-treated with a surface active agent or solvent, if necessary, to render it more hydrophilic and to promote rapid uptake of the liquid sample. Suitable materials for a macroporous carrier include plastics materials such as polyethylene and polypropylene, or other materials such as paper or glass-fibre. In the case that the labelled binding reagent is labelled with a detectable particle, the macroporous body may have a pore size at least ten times greater than the maximum particle size of the particle label. Larger pore sizes give better release of the labelled reagent. As an alternative to a macroporous carrier, the labelled binding reagent may be provided on a non-porous substrate provided upstream from the detection zone, said non-porous substrate forming part of the flow-path.

The porous carrier may comprise a glass-fibre macroporous carrier provided upstream from and overlapping at its distal end a nitrocellulose porous carrier.

The assay device typically comprises a housing containing the assays. The housing may be fluid impermeable and constructed from a suitable plastics material, such as ABS. The assay may further comprise a sample receiving member for receiving the fluid sample. The sample receiving member may extend from the housing.

The housing may be constructed of a fluid impermeable material. The housing will also desirably exclude ambient light. The housing or casing will be considered to substantially exclude ambient light if less than 10%, preferably less than 5%, and most preferably less than 1%, of the visible light incident upon the exterior of the device penetrates to the interior of the device. A light-impermeable synthetic plastics material such as polycarbonate, ABS, polystyrene, polystyrol, high density polyethylene, or polypropylene containing an appropriate light-blocking pigment is a suitable choice for use in fabrication of the housing. An aperture may be provided on the exterior of the housing which communicates with the assay provided within the interior space within the housing. Alternatively the aperture may serve to allow a porous sample receiver to extend from the housing to a position external from the housing.

The assay device may further comprise one or more measurement overflow parameters, wherein if any of the measurements is greater or much less than a value that would have been expected, the result will be rejected. This enables the assay device to reject for example, hardware failures such as a break or shorting in the circuit board, a flat battery, a blocked optical window, a failed LED and so on.

The various analyte and control threshold values may be stored in the device or reader.

The control line signal has been shown to vary over time during the course of the assay measurement. Variation in the control signal over time may be due to various factors, such as the time taken for signal development to occur at the control zone, the amount of labelled binding reagent present and the analyte concentration. An assay device typically comprises an excess of labelled binding reagent such that upon running the test and contacting a liquid sample with the labelled reagent, a large amount of labelled reagent is initially released and travels along the porous carrier towards the detection and control zones. The release profile of labelled reagent changes with respect to time and after the initial high release of labelled reagent decreases in amount. Labelled reagent passing the control zone as well as labelled reagent immobilised at the control zone is measured and thus the amount of labelled reagent detected at the control zone varies over time.

In order to measure an analyte concentration over a certain range it is important to ensure that there is sufficient labelled binding reagent present such that the assay signal does not become saturated. Measurement of large amounts of analyte often requires a corresponding increase in the amount of labelled binding reagent to avoid the so-called "hook effect" or saturation of the assay signal with increasing analyte concentration. Variation in the control signal has been shown to occur particularly in the case where there is an increased amount of binding reagent present, such as in an assay device to measure levels of analyte over an extended or higher concentration range.

It is an advantageous feature of an assay device to be able to provide an "early" result (i.e. before the full signal development time for the assay has elapsed). An example is a pregnancy or drugs of abuse assay test wherein the assay device provides an indication of either the presence or absence of the analyte with respect to a threshold value, which threshold value may be zero.

In the case where a single control threshold is provided, it is possible that the control signal may be greater than the control threshold at an early stage of the assay measurement but less than the control threshold at a later stage of the assay measurement. This provides the possibility that an assay would be considered as having been carried out satisfactorily has an assay result been declared at that early stage of the assay measurement but would not have been considered to have been carried out satisfactorily had the assay result been declared at a later stage of the assay measurement. Therefore, the possibility exists that an assay device having a single control threshold may be incorrectly considered as having been carried out satisfactorily. An assay device or reader comprising more than one threshold reduces the possibility of this error occurring.

An assay device or reader comprising a variable control threshold whose value varied with respect to time or comprising greater than two control thresholds may reduce the possibility of this error in determining the assay to have been carried out satisfactorily even further. However, the larger the number of thresholds, the larger the amount of storage space on the CPU or chip is required and thus the higher the cost of the reader or assay device. Such devices are typically designed to be single use and therefore disposable. Thus, it is advantageous to keep the cost of the device as low as possible whilst maintaining an acceptable level of accuracy.

Furthermore, the signal observed at the control zone has been shown to deteriorate over time with storage of some assay devices. It has also been observed that the signal at the control zone may vary with analyte concentration. For example, in the measurement of hCG concentrations, a decrease in the control signal was observed at around 50,000 mIU/ml. At concentrations higher than 50,000 mIU/ml, the control signal was observed to increase. Thus it is advantageous to provide two control thresholds that differ in value.

According to an embodiment, the assay device is capable of measuring analyte at a higher analyte range. There are several ways of providing such a device.

For example, the assay device may comprise a labelled binding reagent for the analyte and a second binding reagent for the analyte, provided upstream from the detection zone. The second binding reagent serves to remove excess analyte and lower the sensitivity of the assay. This has the effect of increasing the dynamic range of the assay enabling measurement at higher analyte levels. The second binding reagent may be may be immobilised, mobilisable or both. The second binding reagent may be provided at either the same region of the porous carrier as the mobilisable labelled binding reagent, upstream from it or downstream from it. The second binding reagent may bind to the same binding region of the analyte as the mobilisable labelled binding reagent or to a different region of the analyte than the labelled binding reagent. The second reagent may have a different affinity for the analyte than the mobilisable labelled binding reagent of the second assay. In an exemplary embodiment, the second binding reagent has a higher affinity for the analyte than the mobilisable binding reagent of the second assay. The amount of second binding reagent may be varied to change the sensitivity of the assay to analyte concentration. Increasing the amount of second binding reagent present lowers the sensitivity of the assay due to the fact that the second binding reagent is able to bind more analyte, effectively lowering the proportion of labelled binding reagent that is able to bind to the detection zone.

In order to increase the dynamic range of the assay, the assay device may for example comprise multiple detection zones, wherein each detection zone is capable of binding analyte at different analyte concentration levels. For example the respective zones may comprise binding reagent for the analyte having a differing affinities for the analyte.

Other ways to increase the dynamic range of the assay are to provide an assay device comprising a sandwich binding assay and a competition or inhibition assay. For example, the sandwich assay may be the high sensitivity assay, namely it is capable of measuring analyte at a lower concentration range and the inhibition or competition assay may be a low sensitivity assay, namely it is capable of measuring analyte at a higher concentration range. A further way is to alter the affinity or amount of the labelled binding reagent or the immobilised reagent at the detection zone. A high affinity binding reagent will have a higher analyte sensitivity than a lower affinity binding reagent. Similarly a low concentration of binding reagent will have a lower analyte sensitivity than a high concentration of binding reagent. The assay sensitivity can be changed by altering the ratio of binding reagent to the label of the labelled binding reagent. If a particle is used as the label, then the quantity of the binding reagent applied to the label can be altered to alter assay sensitivity. A further way to manipulate the sensitivity of an assay is to vary the quantity of the label used in the assay. For example the sensitivity of an assay may be lowered by reducing the ratio of binding reagent to labelled species for the labelled binding reagent.

A further means of manipulating the sensitivity of an assay is to alter the optical density of a label. The assay sensitivity can be lowered by use of a label with a low optical density. This may be achieved for example by provision of a polymer particle label having a low concentration of dye or by use a coloured label which is less sensitive to an optical detector.

Yet a further way to measure high analyte levels is to employ a non-particulate labelled binding reagent. High levels of analyte when measured by way of a sandwich binding assay require high levels of binding reagent. In the case wherein the label is a particle label, provision of high levels of analyte within or on the porous carrier can give rise to steric hindrance resulting in poor assay sensitivity. Conversely, at lower analyte levels, the use of a non-particle labelled binding reagent can give rise to a low signal due to the low optical density. However, at high analyte levels, non-particle labels may be present at sufficiently high levels to be readily detected. An example of a optically detectable non-particulate label may be a dye. The dye may be fluorescent.

Assay sensitivity may be influenced by the flow rate of the porous carrier. A way to lower the sensitivity of the assay is to employ a porous carrier (such as nitrocellulose) having a higher flow rate.

The sensitivity of an assay may be further manipulated by modifying the rate at which the labelled binding reagent is released from its origin. A further way to lower analyte sensitivity is to provide for a rapid release of the labelled binding reagent from the porous carrier during contact with the liquid sample. The release of the labelled binding reagent can be modified by the provision of sugars, proteins or other polymeric substances such as methylcellulose within the device.

According to a particular embodiment, the assay device comprises a mobilisable second binding reagent for the analyte and a mobilisable binding reagent for the analyte provided upstream from the detection zone. The second binding reagent may be provided at the same or similar position upstream from the detection zone as the labelled binding reagent.

According to a particular embodiment, the assay device comprises two assays each comprising an flow-path, wherein the first assay is capable of measuring analyte in a lower analyte concentration range and the second assay is capable of measuring analyte in a higher analyte concentration range. The first assay may comprise a reference zone and the second assay may comprise a control zone.

The assay device of the invention may be used to measure the extent or presence of hCG over an extended concentration range. The range may vary from between about 10 mIU to about 250,000 mIU.

The second assay may comprise a labelled binding reagent for the analyte and a second binding reagent for the analyte. The first assay may comprise labelled binding reagent for the analyte provided upstream from the detection zone.

The assay device may comprise one or more further measurement threshold values to indicate the level of analyte in a certain analyte range. In an embodiment, the assay device comprises a first and second measurement thresholds, wherein an analyte measurement signal of less than the first measurement threshold is indicative of the absence of analyte or the absence of analyte above a certain level and wherein an analyte measurement signal greater than the second threshold is indicative of the level of analyte in a second concentration range and a measurement signal of less than the second threshold is indicative of the level of analyte in a first concentration range. According to a particular embodiment, the assay device additionally comprises a third measurement threshold, wherein an analyte measurement signal greater than the third threshold is indicative of the level of analyte in a third concentration range.

In particular the assay device may be capable of measuring the presence and extent of the analyte hCG analyte in a liquid sample, in particular urine, of a female mammalian subject. The assay device may comprise a first measurement threshold, wherein hCG analyte signal levels of below the threshold are indicative or being not pregnant and wherein hCG analyte signal levels greater than or equal to the first measurement threshold are indicative of being pregnant, wherein the device comprises at least a further measurement threshold. In addition the assay device may provide an indication of the extent of pregnancy. The assay device may provide a time-based indication to the user, such as the extent of pregnancy in units of days or weeks.

A typical full assay development time for an assay test for the determination of hCG in urine is 3 minutes.

For the avoidance of doubt, it is hereby expressly stated that any feature described herein as "preferred", "advantageous", "convenient" or "desirable and the like may be present in the invention in isolation, or in any combination with any one or more other features so described herein, unless the context dictates otherwise.

Aspects of the invention are further illustrated by reference to the following figures:

BRIEF DESCRIPTION OF THE FIGURES

FIGS. 1b and 1c show the variation in control signal over time for assay devices prepared according to Examples 1 and 2 below;

FIG. 1a shows a typical variation in the control signal with respect to time of running the assay. Also shown are three threshold values, 20%, 30% and 40%. In the case where just a single threshold were employed, for example 30% A, the control signal is greater than the threshold at t=40 s but less than the threshold at the full assay development time of 150 s. In this case, had a result been declared early at t=40 s, the assay device would incorrectly interpret the control as having been valid, because the determination of whether a control signal is valid for this case would require that the assay signal be greater than 30% A at the full assay development time. If however a single control zone threshold were employed at 40%, then an assay test having a control signal value of 40% A at t=40 s and 32% A at the full assay development time of 150 s for which the control was valid would be unnecessarily determined as being not valid. Thus in the latter case an assay would be rejected unnecessarily. Thus, in summary, the control signal value may vary with time (and in particular may decrease, rather than remain constant, once a peak signal value has been obtained), and in order to reflect this the invention provides an assay device with a control signal threshold that may vary with time. For example, in one embodiment of an assay device in accordance with the invention employs two control thresholds, a first threshold corresponding to a first assay decision time and a second threshold at a second assay decision time. Due to the initial rise in labelled reagent at t=40 s, a first control threshold is employed which is greater than the second control threshold at t=150 s. The lower control threshold needs to take into account aging effects of the assay device as well as any potential decrease in the control signal at particular analyte concentrations such that these assays are not unnecessarily rejected.

Figure 2:
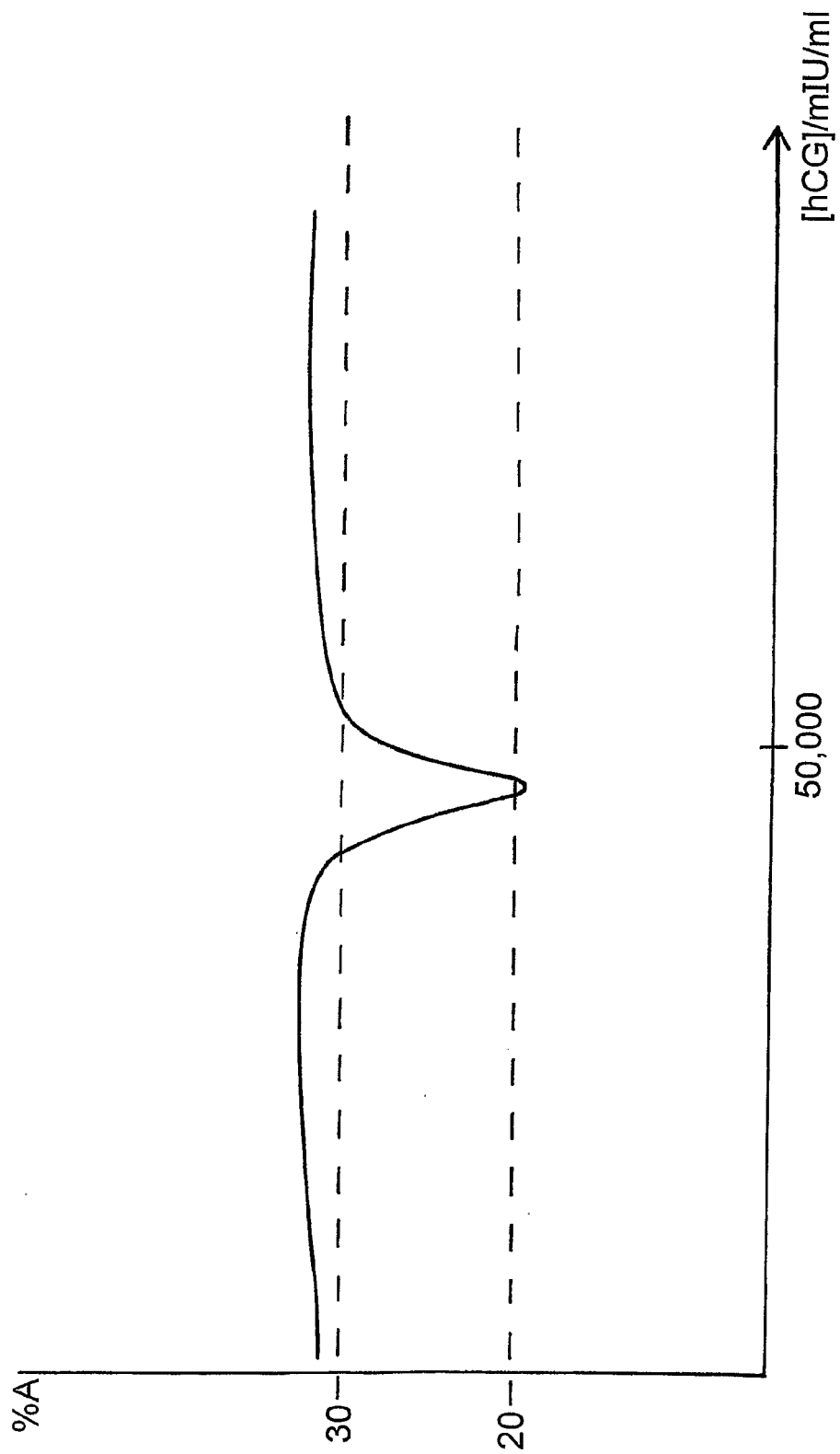
FIG. 2 shows an example of the observed variation in control signal as a function of hCG concentration at the full development time of the assay (t=150 s)

In the case of hCG measurement, a decrease in the control signal value was unexpected shown to occur at around 50,000 mIU/ml. At values greater than around 50,000 mIU/ml, the control signal subsequently increased in value. The signal observed at the control zone vs. hCG concentration at the full development time of t=150 s is shown in FIG. 2. Thus values obtained at the control zone for levels of hCG of around 50,000 mIU/ml may be less than a control threshold and thus result in an assay device that is classified as not being valid. It is therefore necessary to employ a control line threshold which is sufficiently low to take into account of any decrease in control line signal at a particular analyte concentration as well as take into account any decrease in assay control signal due to aging of the device.

Figure 3A:
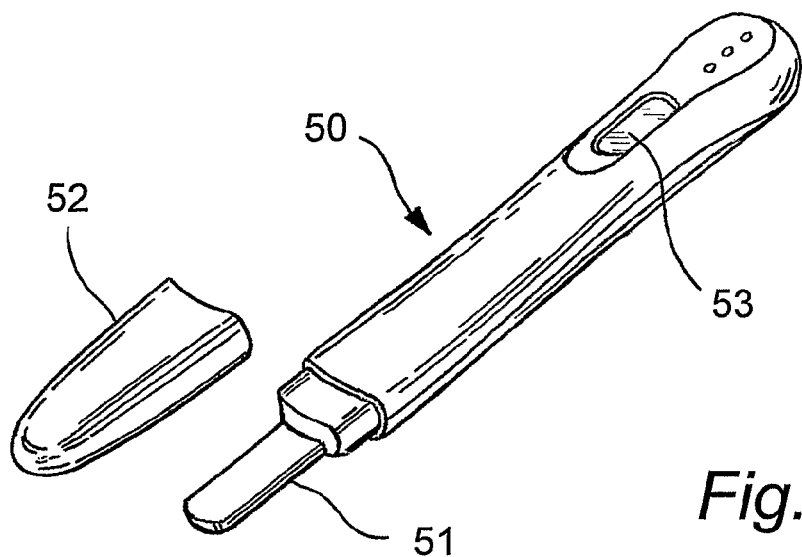
FIGS. 3a and 3b show a typical embodiment of an assay device of the invention

FIG. 3a shows a typical assay device according to an embodiment of the invention. The device is elongate having a length of about 14 cm and a width of about 25 mm, comprising housing (50), a porous sample receiver (51) and an LCD display (53) for displaying the results of the assay. Also provided within the assay device and not shown are the assay flow-paths, optical means, a power source and associated electronic components. The assay device may also have a removable cap (52) to fit over the porous sample receiver.

Figure 3B:
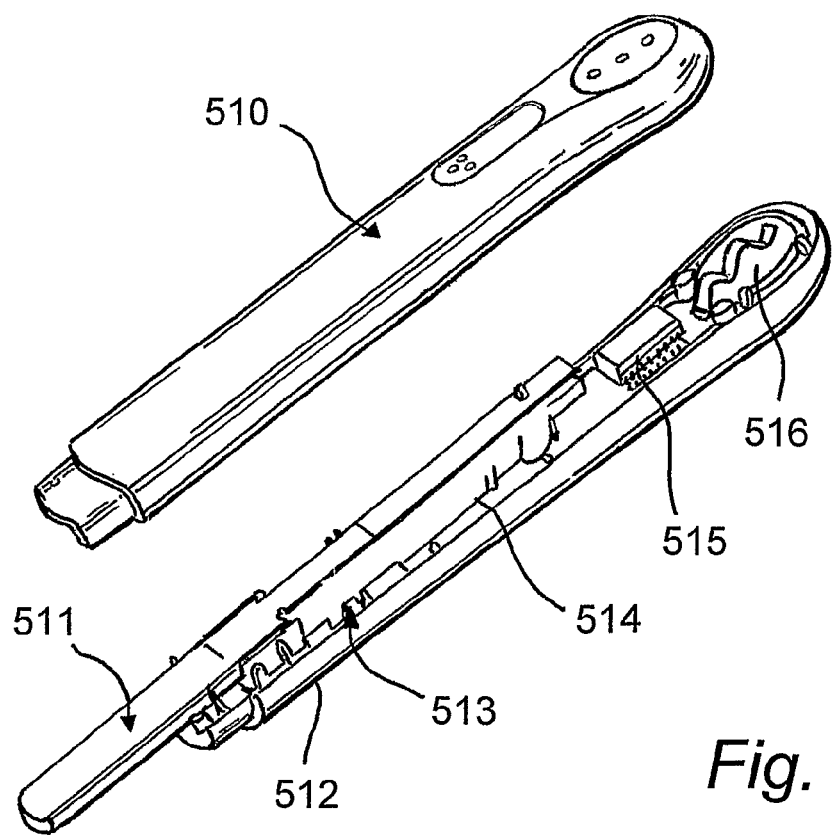

FIG. 3b is an exploded view of the device shown in FIG. 3a. The device comprises upper and lower housing components (510, 512), a desiccant tablet (513) to maintain low levels of humidity within the device, a battery (516) an optical baffle (514) and computer chip (515).

EXAMPLE 1

Preparation of a high sensitivity assay device A high sensitivity assay device was was prepared for the determination of hCG analyte comprising a mobilisable labelled binding reagent for hCG provided upstream on a glass fibre porous carrier from a detection zone and a control zone provided on a nitrocellulose porous carrier, the detection zone comprising immobilised binding reagent for hCG.

The detection zone was prepared by dispensing a line of anti-β-hCG antibody (in-house clone 3468) at a concentration of 3 mg/ml in PBSA buffer, at a rate of 1 μl/cm on onto bands of nitrocellulose of dimensions 350 mm length×40 mm width (Whatman) having a pore-size of 8 microns and a thickness between 90-100 microns which had been laminated to a 175 micron backing layer. The anti-β-hCG antibody was applied using the Biodot xyz3050 dispensing platform as a line ~1.2 mm in width and ~300 mm in length at a position of 10 mm along the length of the nitrocellulose.

The control zone was prepared plotting goat-anti-rabbit antibody (Lampire), 2 mg/ml in PBSA buffer at 1 μl/cm onto nitrocellulose at the 13 mm position, 3 mm downstream of the detection zone, using a Biodot XYZ3050 dispensing platform.

The bands of NC were dried using Hedinair drying oven serial #17494 set at 55° C. and speed 5 (single pass). The NC was then blocked using a blocking buffer comprising a mixture of 5% ethanol (BDH Analar 104766P) plus 150 mM Sodium Chloride (BDH Analar 10241AP) plus 50 mM trizma base from (Sigma T1503) plus Tween 20 (Sigma P1379) and 1% (w/v) polyvinyl alcohol (PVA, Sigma 360627). The blocking buffer was applied at a rate of 1.75 μl/mm to the proximal end of the band. Once the blocking solution had soaked into the membrane a solution of 2% (w/v) sucrose (Sigma S8501 in deionised water) was applied using the same apparatus at a rate of 1.6 μl/mm and allowed to soak into the nitrocellulose membrane for ~5 minutes). The bands of NC were then dried using a Hedinair drying oven serial #17494 set at 75° C. and speed 5 (single pass).

Preparation of the Labelled Binding Reagent for the Analyte.

Labelled binding reagent was prepared according to the following protocol:

Coating Latex Particles with Anti-α hCG

1. Dilute blue latex particles from Duke Scientific (400 nm in diameter, DB1040CB at 10% solids (w/v)) to 2% solids (w/v) with 100 mM di-sodium tetra borate buffer pH 8.5 (BDH AnalaR 102676G) (DTB).
2. Wash the diluted latex by centrifuging a volume of (2 mls) of diluted latex in two Eppendorf centrifuge tubes at 17000 rpm (25,848 rcf) for 10 minutes on an Heraeus Biofuge 17RS centrifuge. Remove and discard the supernatant and re-suspend the pellets in 100 mM DTB to give 4% solids (w/v) in a total volume of 1 ml.
3. Prepare a mixture of ethanol and sodium acetate (95% Ethanol BDH AnalaR 104766P with 5% w/v Sodium Acetate Sigma S-2889).
4. Add 100 μls ethanol-sodium acetate solution to the washed latex in step 2 (this is 10% of the volume of latex).
5. Dilute the stock antibody (in-house clone 3299) to give ~1200 m/ml antibody in DTB.
6. Heat a volume of 1 ml of the diluted antibody from step 5 in a water bath set at 41.5° C. for ~2 minutes. Also heat the washed latex plus ethanol-sodium acetate from step 4 in the same water bath for 2 minutes.
7. Add the diluted antibody to the latex plus ethanol-acetate, mix well and incubate for 1 hour in the water bath set at 41.5° C. whilst mixing using a magnetic stirrer and a magnetic flea placed in the mixture.
8. Prepare 40 mg/ml Bovine Serum Albumin (BSA) Solution (Intergen W22903 in de-ionised water). Block the latex by adding an equal volume of 40 mg/ml BSA to the mixture of latex/antibody/ethanol-acetate and incubate in the water bath at 41.5° C. for 30 minutes with continued stirring.
9. Centrifuge the mixture at 17000 rpm for 10 minutes as in step 2, (split the volume into 1 ml lots between Eppendorf tubes). Remove and discard the supernatant and re-suspend the pellet in 100 mM DTB. Repeat the centrifugation as in step 2, remove and discard the supernatant and re-suspend in pellet in Air Brushing Buffer (20% (w/v) Sucrose Sigma S8501, 10% BSA (w/v) in 100 mM Trizma Base Sigma T1503 pH to 9). Add Air Brushing Buffer to give 4% solids (w/v) latex.

The conjugated latex was and sprayed in a mixture of BSA and sucrose onto a glass-fibre porous carrier (F529-09, Whatman) at a rate of 50 g/hr and 110 mm/s and dried using a Hedinar Conveyor Oven Serial number 17494 set at 65° C. and speed 5 (single pass).

Labelled binding reagent for the control zone was also deposited onto the same region of the porous carrier as the labelled binding reagent for the analyte as follows:

Rabbit IgG (Dako) was conjugated to 400 nm blue latex polystyrene latex (Duke Scientific) in BSA/sucrose to give a final % blue latex of 0.7% solids and sprayed at 65 g/hr onto glass fibre.

The glass fibre material with sprayed labelled binding reagent was attached to the nitrocellulose membrane using a clear adhesive coated laminate film (Ferrisgate, 38 mm wide) arranged such that the labelled reagent was uppermost and the glass fibre overlapped the surface of the nitrocellulose by ~2 mm along the length (350 mm) of the band of nitrocellulose membrane. The glass fibre was attached to the end of the nitrocellulose such that it was upstream of the detection zone.

The laminated sheet was subsequently cut into test-strips of 6 mm width.

EXAMPLE 2

Preparation of a Low Sensitivity Scavenger Assay Device for the Determination of hCG Analyte Comprising a Mobilisable Labelled Binding Reagent for hCG and a Mobilisable Unlabelled Binding Reagent for hCG Provided Upstream from a Detection and Control Zone The detection zone and control zones were prepared according to Example 1.
Preparation of the Mobilisable Labelled and Unlabelled Binding Reagents Mouse-anti-human α-hCG mAb (clone 3299) conjugated to 400 nm blue polystyrene latex (Duke Scientific) was mixed with scavenger antibody mAb mouse anti-human β-hCG (in-house clone 3468) at 3 mg/ml to give a final % blue latex of 3%, a final 3468 concentration of 0.075 mg/ml and 0.06 mg/ml concentration of the free anti-β hCG antibody. The resulting mixture was airbrushed onto Whatman glass fibre (F529 25 mm wide reels) using the BIODOT XYZS (serial number 1673) at 90 g/hr sprayed at 2.02 μg/cm onto F529-09 glass fibre.

Labelled binding reagent for the control zone was also deposited onto the same region of the porous carrier as the labelled binding reagent for the analyte according to Example 1.

The glass fibre was dried using a Hedinar Conveyor Oven Serial number 17494 set at 65° C. and speed 5 (single pass). A second pass of latex was deposited onto the glass fibre by repeating the above however at an offset of ~0.8 mm from the original position of spray (further downstream of the glass fibre). The glass fibre as dried as described above.
Measurement of the Variability in Control Signal with Time.

An assay device prepared according to Example 1 was tested with 0 mIU/ml hCG in buffer and the control signal measured over time as well as the signal at a reference zone which was chosen as a zone situated upstream from the detection zone. Values are presented in terms of % A, namely the signal at the control zone with respect to that of the signals measured at the reference zone.

Figure 1A:
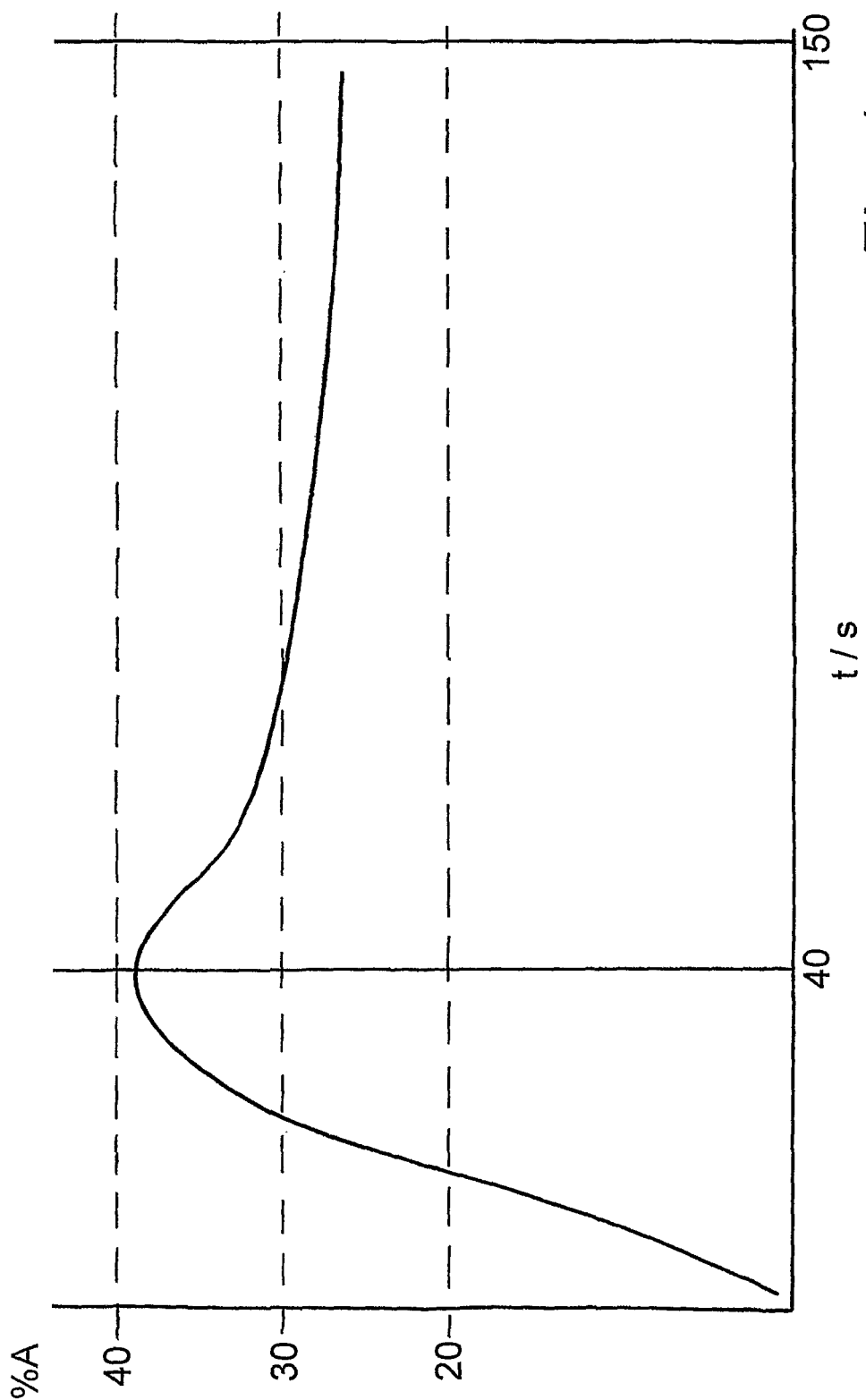
FIG. 1a shows a graph giving an example of the variation in control signal over time.
Figure 1B:
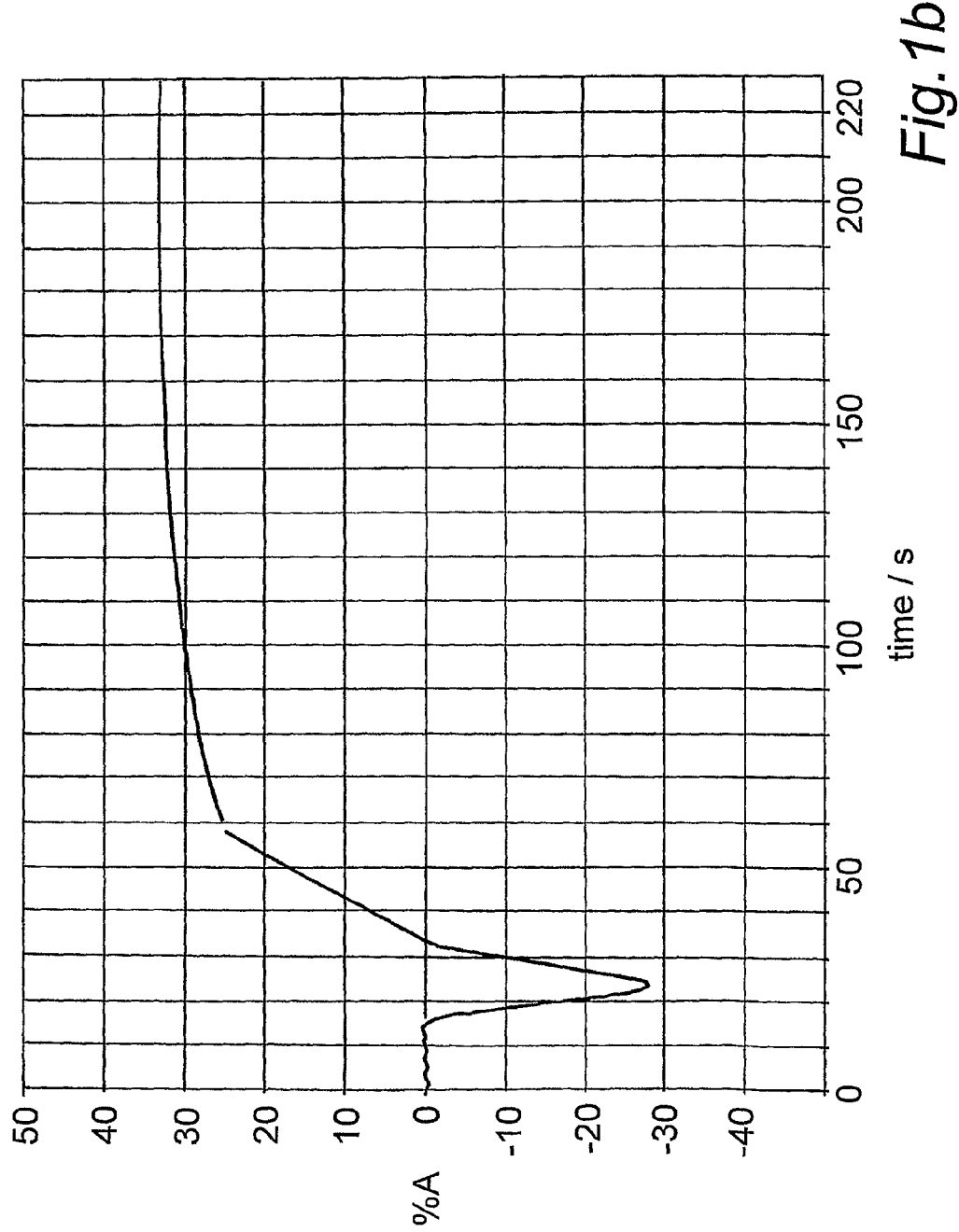

An assay device prepared according to Example 2 was tested with 100 mIU/ml in buffer and the control signal measured over time. Values are presented in terms of % A, namely the signal at the control zone with respect to that of the signals measured at the control zone. The reference values by which the control signals were referenced were obtained by testing an assay device according to that Example 1 with 100 mIU/ml in buffer. The variation in signal values are shown in FIGS. 1b and 1c.

It may be seen that the control signal according to that of Example 1 shows less variability over time compared to that of Example 2.

Assay devices prepared according to Example 2 were tested with liquid samples containing analyte and their analyte measurement and control signals measured over time. Two sets of measurements were carried out comparing the use of a single control threshold value of 30% A to two control threshold values of 20% A and 40% A. The % A value of the control signal was only considered 40 seconds after flow was detected in the high sensitivity test window which corresponded to between 50 and 60 seconds from calibration. The full development time of the assay, $t_{fd}$, was 180 s. At times $t<t_{fd}$, the control signal was compared to the 40% A control threshold value and at a time $t=t_{fd}$, the control signal was compared to the 20% A control threshold value. Tested assay devices were also compared to a single control threshold of 30% A at a time $t=t_{fd}$. It was seen that assay devices measured with respect to two control threshold values had a higher percentage of being correctly classified that the assay had been carried out satisfactorily than those assay devices measured with respect to a single control threshold value.

The invention claimed is:
1. An assay result reading apparatus, for reading the result of an assay, comprising:
 a) first and second control thresholds;
 b) a data processing means for processing an analyte measurement signal indicative of the presence and/or amount of an analyte; and for processing a control signal indicative of whether the assay has been carried out satisfactorily; to:

up until a time $t_1$ after commencement of the assay measurement, to compare the control signal with the first control threshold and determine that the assay has been carried out satisfactorily if the control signal exceeds or is equal to the first control threshold, and if the control signal is less than the first control threshold to continue the assay measurement; and at a time $t > t_1$ to compare the control signal with a second control threshold and provide an assay result if the control signal exceeds or is equal to the second control threshold.

2. An assay device for providing the presence and/or amount of an analyte in a liquid sample comprising:
   a) an assay result reading apparatus according to claim 1; and
   b) one or more assay flow-paths along which a liquid sample may flow, said one or more flow paths comprising: a detection zone for immobilizing a labelled binding reagent indicative of the presence and/or amount of the analyte; and a control zone for indicating that assay has been carried out satisfactorily.

3. The assay device or reader according to claim 1 wherein the first control threshold is greater than the second control threshold.

4. The assay device or reader according to claim 1 comprising an assay timing means for timing the measurement of the assay.

5. The assay device according to claim 2 comprising mobilizable labelled binding reagent for the analyte capable of being immobilized at the control zone.

6. The assay device according to claim 2 comprising an optical illumination and detection means for illuminating and detecting labelled binding reagent at the detection and control zones.

7. The assay device according to claim 2, wherein the one or more flow-paths further comprises a reference zone.

8. The assay device or reader according to claim 1, wherein the control signal is compared to the second control threshold at time $t = t_{fd}$, and compared to the first control threshold at time $t < t_{fd}$.

9. The assay device or reader according to claim 1 further comprising a minimum assay development time, $t_{md}$, wherein $t_1 \geq t_{md}$.

10. The assay device according to claim 2 comprising mobilizable labelled binding reagent for the analyte and a second binding reagent for the analyte provided upstream from the detection zone.

11. The assay device according to claim 2 comprising two assay flow paths each comprising a detection zone for the analyte.

12. The assay device according to claim 11 wherein the first assay flow-path is capable of measuring an analyte in a lower analyte concentration range and the second assay flow-path is capable of measuring the analyte in a higher concentration range.

13. The assay device according to claim 12 wherein the first assay comprises mobilizable labelled binding reagent for the analyte provided upstream from the detection zone and the second assay comprises mobilizable labelled binding reagent for the analyte and a second binding reagent for the analyte provided upstream from the detection zone.

14. The assay device according to claim 11, wherein the amount of labelled binding reagent in the second assay is greater than in the first assay.

15. The assay device according to claim 11, wherein the flow-path of the first assay comprises a reference zone and the flow-path of the second assay comprises a control zone.

16. The assay device according to claim 10, wherein the second binding reagent for the analyte is mobilizable.

17. The assay reader or device according to claim 1, wherein the analyte is hCG.

18. The assay reader or device according to claim 1, wherein the liquid sample is urine.

19. The assay reader or device according to claim 1 for the measurement of hCG in a female mammalian subject, comprising a measurement threshold indicative of a pregnant or not pregnant condition, wherein an analyte measurement signal of greater than or equal to the measurement threshold is indicative that the subject is pregnant and wherein an analyte measurement signal less than the measurement threshold is indicative that the subject is not pregnant.

20. The assay reader or device according to claim 18 further comprising a second measurement threshold indicative of the extent of pregnancy, wherein a signal measurement value of greater than the second measurement threshold is indicative of the extent of pregnancy in a second range and wherein a signal measurement value of less than the second measurement threshold and greater than the first measurement threshold is indicative of the extent of pregnancy in a first range.

21. The assay device according to claim 2, wherein the flow path comprises a porous carrier.

22. The assay device according to claim 20 wherein the porous carrier comprises first and second porous carrier materials which overlap each other.

23. The assay device according to claim 21 wherein the first porous carrier comprises labelled binding reagent and the second porous carrier comprises the detection zone.

24. A method of determining the result of an assay comprising:
   a) measuring an analyte measurement signal indicative of the presence and/or amount of an analyte and a control signal indicative of whether the assay has been carried out satisfactorily;
   b) up until a time $t_1$ after commencement of the assay measurement, determining that the assay has been carried out correctly if the control signal exceeds or is equal to a first control threshold and if the control signal is less than the first control threshold to continue the assay signal measurement; and at a time $t > t_1$ to compare the control signal with a second control threshold and provide an assay result if the control signal exceeds or is equal to the second control threshold.

25. An assay result reading apparatus, for reading the result of an assay comprising:
   a) A variable control threshold whose value varies over the time of the assay measurement;
   b) a data processing means for processing an analyte measurement signal over time indicative of the presence and/or amount of an analyte; and for processing a control signal over time indicative of whether the assay has been carried out satisfactorily; to: at any particular time during measurement of the assay to compare the control signal with the variable control threshold and determine that the assay has been carried out satisfactorily if the control signal exceeds or is equal to the variable control threshold.

26. An assay device for providing the presence and/or amount of an analyte in a liquid sample comprising: a) an assay result reading apparatus according to claim 25; and one or more flow-paths along which a liquid sample may flow, said one or more flow paths comprising: a detection zone for immobilizing a labelled binding reagent indicative of the presence and/or amount of the analyte; and a control zone for indicating that assay has been carried out satisfactorily.

\* \* \* \* \*